US00PP31666P2

(12) United States Plant Patent
Winslow

(10) Patent No.: US PP31,666 P2
(45) Date of Patent: Apr. 14, 2020

(54) ***LOBULARIA* PLANT NAMED 'BALBEEZURP'**

(50) Latin Name: *Lobularia maritima*
Varietal Denomination: Balbeezurp

(71) Applicant: Ball Horticultural Company, West Chicago, IL (US)

(72) Inventor: Benjamin K. Winslow, Austin, TX (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 16/501,925

(22) Filed: Jul. 3, 2019

(51) Int. Cl.
*A01H 5/02* (2018.01)
*A01H 6/20* (2018.01)

(52) U.S. Cl.
USPC ..... Plt./263.1
CPC ..... *A01H 6/20* (2018.05)

(58) Field of Classification Search
USPC ..... Plt./263.1
CPC ..... A01H 5/02
See application file for complete search history.

*Primary Examiner* — Kent L Bell
(74) *Attorney, Agent, or Firm* — Audrey Charles

(57) ABSTRACT

A new and distinct cultivar of *Lobularia* plant named 'Balbeezurp', characterized by its medium purple-colored flowers, dark green-colored foliage, moderately vigorous, mounded-spreading growth habit, is disclosed.

1 Drawing Sheet

Latin name of genus and species of plant claimed: *Lobularia maritima.*

Variety denomination: 'Balbeezurp'.

BACKGROUND OF THE INVENTION

The present invention relates to a new and distinct cultivar of *Lobularia* plant botanically known as *Lobularia maritima* and hereinafter referred to by the cultivar name 'Balbeezurp'.

The new cultivar originated in a controlled breeding program in Arroyo Grande, Calif. during January 2013. The objective of the breeding program was the development *Lobularia* cultivars that have a densely branched and moderately vigorous, mounded-spreading growth habit.

The new *Lobularia* cultivar is the result of cross-pollination. The female (seed) parent of the new cultivar is 'Easter Bonnet Violet', not patented, characterized by its dark purple-colored flowers, dark green-colored foliage, low growth vigor and mounded-spreading growth habit. The male (pollen) parent of the new cultivar is Lavender Stream 'DLOBU22', U.S. Plant Pat. No. 25,141, characterized by its light purple-colored flowers, medium green-colored foliage, and moderately vigorous, semi-trailing, compact and dense habit. The new cultivar was discovered and selected as a single flowering plant within the progeny of the above stated cross-pollination during July 2013 in a controlled environment in Arroyo Grande, Calif.

Asexual reproduction of the new cultivar by terminal stem cuttings since July 2013 in Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balbeezurp' as a new and distinct cultivar of *Lobularia* plant:

1. Medium purple-colored flowers;
2. Dark green-colored foliage;
3. Moderately vigorous, mounded-spreading growth habit.

Plants of the new cultivar differ from plants of the female parent primarily in having a lighter shade purple flower color, and a more vigorous growth habit. Plants of the new cultivar differ from plants of the male parent primarily in having a darker shade of purple flower color, and a darker shade of green foliage color.

Of the many commercially available *Lobularia* cultivars, the most similar in comparison to the new cultivar is Dark Knight 'INLOBU1007', U.S. Plant Pat. No. 26,931. However, in comparison, plants of the new cultivar differ from plants of 'INLOBU1007' in at least the following characteristics:

1. Plants of the new cultivar have lighter purple-colored flowers than plants of 'INLOBU1007';
2. Plants of the new cultivar have less growth vigor than plants of 'INLOBU1007'; and
3. Plants of the new cultivar are shorter than plants of 'INLOBU1007'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balbeezurp'. The plants were approximately 4 months old and grown in 4.5-inch pots for approximately 10 weeks in a greenhouse in West Chicago, Ill. Plants were given one pinch one week prior to transplant.

DETAILED BOTANICAL DESCRIPTION

Figure 1:
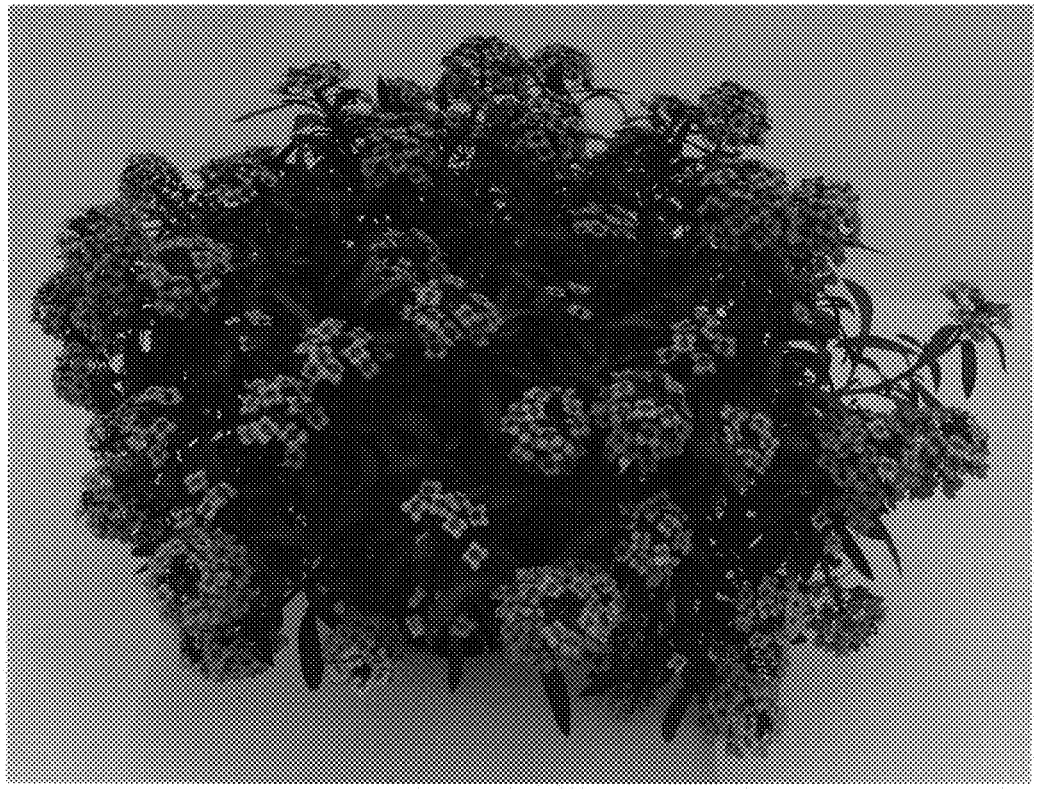
FIG. 1 illustrates a side view of the overall growth and flowering habit of 'Balbeezurp'.
Figure 2:
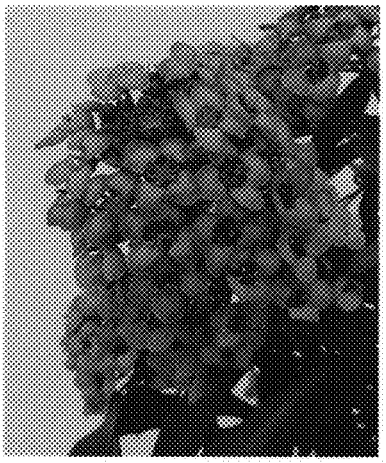
FIG. 2 illustrates a close-up view of the inflorescences of 'Balbeezurp'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in March 2019 under natural light conditions in West Chicago, Ill.

The following descriptions and measurements describe approximately 4-month old plants produced from cuttings from stock plants and grown in a glass-covered greenhouse under conditions comparable to those used in commercial practice. The plants were grown in West Chicago, Ill. in 4.5-inch pots for approximately 10 weeks utilizing a soilless growth medium. Plants were given one pinch one week prior to transplant. Greenhouse temperatures were maintained at approximately 67° F. to 72° F. (19° C. to 22° C.) during the day and approximately 65° F. to 68° F. (18° C. to 20° C.) during the night. Supplemental lighting was used. Measurements and numerical values represent averages of typical plants.

Botanical classification: *Lobularia maritima* 'Balbeezurp'.

Parentage:

*Female parent*.—'Easter Bonnet Violet', not patented.

*Male parent*.—Lavender Stream 'DLOBU22', U.S. Plant Pat. No. 25,141.

Propagation:

*Type cutting*.—Terminal stem.

*Time to initiate roots*.—Approximately 6 to 9 days.

*Time to produce a rooted cutting*.—Approximately 21 to 28 days.

*Root description*.—Fine, fibrous.

*Rooting habit*.—Freely branching.

Plant description:

*Commercial crop time*.—Approximately 4 to 5 weeks from a rooted cutting to finish in a 10 cm pot.

*Growth habit and general appearance*.—Annual, moderately vigorous, mounded-spreading.

*Size*.—Height from soil level to top of plant plane: Approximately 10.0 cm. Width: Approximately 29.0 cm.

*Branching habit*.—Freely branching, pinching improves basal branching. Quantity of main branches per plant: Approximately 5.

*Branch*.—Shape: Rounded and slightly ribbed. Strength: Strong, flexible. Length to base of inflorescence: Approximately 8.5 cm. Diameter: Approximately 2.5 mm. Length of central internode: Approximately 1.0 cm. Texture: Densely pubescent with appressed hairs. Color of young stems: 144A. Color of mature stems: 146C.

Foliage description:

*General description*.—Quantity of leaves per main branch: Approximately 14. Fragrance: None detected. Form: Simple. Arrangement: Alternate.

*Leaves*.—Aspect: Petiole at acute angle to stem, tips downward turning with age. Shape: Oblanceolate. Margin: Entire. Apex: Acute. Base: Attenuate. Venation pattern: Pinnate. Length of mature leaf: Approximately 3.0 cm. Width of mature leaf: Approximately 6.0 mm. Texture of upper and lower surfaces: Moderately pubescent with appressed hairs. Color of upper surface of young and mature foliage: 137A with midvein of 146C, other venation indistinguishable. Color of lower surface of young and mature foliage: Closest to 137B with midvein of 146C, other venation indistinguishable.

*Petiole*.—Length: Approximately 7.0 mm. Width: Approximately 2.0 mm. Texture: Moderately pubescent with appressed hairs. Color: 146C.

Flowering description:

*Flowering habit*.—'Balbeezurp' is freely flowering under outdoor growing conditions with substantially continuous blooming throughout the spring.

*Lastingness of individual flower on the plant*.—Approximately 4 to 5 days.

Inflorescence description:

*General description*.—Type: Terminal corymb. Quantity per plant: Approximately 50. Fragrance: Sweetly fragrant. Length or height: Approximately 3.5 cm. Width: Approximately 2.5 cm. Quantity of fully open flowers per inflorescence: Approximately 48.

*Peduncle*.—Strength: Strong, flexible. Length: Approximately 1.0 cm. Diameter: Approximately 2.0 mm. Texture: Glabrous. Color: 146B.

Flower description:

*Type*.—Small, cruciferous flowers, freely flowering, not persistent.

*Bud*.—Rate of opening: Generally takes 2 to 3 days for bud to progress from first color to fully open flower.

*Bud just before opening*.—Shape: Globose. Diameter: Approximately 2.0 mm. Color: Sepals of 146B; petals of 86A.

*Corolla*.—Shape: Cruciform lobes with claws surrounded by calyx. Aspect: Facing upward and outward. Width: Approximately 6.0 cm. Depth: Approximately 2.0 mm.

*Petals*.—Quantity: 4. Shape: Ovate. Margin: Entire. Apex: Obtuse. Base: Attenuate. Length of lobe: Approximately 3.0 cm. Width of lobe: Approximately 3.0 mm. Length of claw: Approximately 1.0 mm. Width of claw: Less than 1.0 mm. Color of upper surface of lobe when first and fully open: N87C mottled with and margins of N87A. Color of lower surface of lobe when first and fully open: N87A with streaks of N87C at base. Color of upper and lower surfaces of claw: 146D tinted with N87A.

*Calyx*.—Shape: Cupped. Diameter: Approximately 3.0 mm.

*Sepals*.—Quantity per flower: 4, distinct. Shape: Elliptic. Margin: Entire. Apex: Acute. Base: Truncate. Length: Approximately 2.0 mm. Width: Approximately 1.0 mm. Texture of inner surface: Glabrous. Texture of outer surface: Moderately pubescent with appressed hairs. Color of inner and outer surfaces: Centers of 146B; margins of 86A.

*Pedicel*.—Strength: Strong, flexible. Aspect: Acute angle to perpendicular to peduncle. Length: Approximately 9.0 mm. Diameter: Less than 1.0 mm. Texture: Densely pubescent with appressed hairs. Color: 146B.

*Reproductive organs*.—Androecium: Stamen quantity: 6 per flower. Stamen length: Approximately 1.5 mm, 1 pair slightly shorter and inserted lower. Filament color: 146D. Anther shape: Bithecous, dorsifixed. Anther color: 16A. Pollen amount: Abundant. Pollen color: 16B. Gynoecium: Pistil quantity: 1 per flower, ovary superior. Pistil length: Approximately 2.0 mm. Stigma shape: Capitate. Stigma color: 145D. Style color: N187A. Style length: Less than 1.0 mm. Ovary length: Approximately 1.5 mm. Ovary texture: Moderately pubescent with appressed hairs. Ovary color: 137B.

Seed and fruit production: Neither seed nor fruit production has been observed.

Disease and pest resistance: Resistance to pathogens and pests common to *Lobularia* has not been observed.

What is claimed is:

1. A new and distinct cultivar of *Lobularia* plant named 'Balbeezurp', substantially as herein illustrated and described.

* * * * *